(12) United States Patent
Maki et al.

(10) Patent No.: US 8,709,821 B2
(45) Date of Patent: Apr. 29, 2014

(54) LUMINESCENT SUBSTRATE FOR LICIFERASE

(75) Inventors: Shojiro Maki, Tokyo (JP); Satoshi Kojima, Tokyo (JP); Haruki Niwa, Tokyo (JP)

(73) Assignees: The University of Electro-Communications, Choufu-Shi (JP); Campus Create Co., Ltd., Setagaya-Ku (JP)

( * ) Notice: Subject to any disclaimer, the term of this patent is extended or adjusted under 35 U.S.C. 154(b) by 593 days.

(21) Appl. No.: 12/865,328

(22) PCT Filed: Feb. 2, 2009

(86) PCT No.: PCT/JP2009/000376
§ 371 (c)(1),
(2), (4) Date: Oct. 25, 2010

(87) PCT Pub. No.: WO2009/096197
PCT Pub. Date: Aug. 6, 2009

(65) Prior Publication Data
US 2011/0033878 A1 Feb. 10, 2011

(30) Foreign Application Priority Data
Feb. 2, 2008 (JP) .................................. 2008-023396

(51) Int. Cl.
*G01N 33/00* (2006.01)

(52) U.S. Cl.
USPC ........................... 436/140; 436/142; 436/172

(58) Field of Classification Search
USPC ......................................... 436/140, 142, 172
See application file for complete search history.

(56) References Cited

U.S. PATENT DOCUMENTS 3,164,597 A 1/1965 Frederick Leonard

FOREIGN PATENT DOCUMENTS

| JP | 47-30183 | 8/1978 |
| JP | 2007-91695 A | 4/2007 |
| WO | WO 2006/130551 A2 | 12/2006 |

OTHER PUBLICATIONS

Molecular Probes, "ATP determination kit", production information, 2005, pp. 1-3.*
Wang et al. "Detection of homocystein and cysteine" J. Am. Chem. Soc., 2005, 127:15949-15958.*
Golinski, M., Prostaglandin photoaffinity probes: Synthesis and binding affinity of aryl azide-substituted C-1 esters of prostaglandin F2α, Eicosanoids, 1992, 5(2), p. 99-107.
Mushkalo, L., D., N-Acylpolymethinecyanines, Khimiya Geterotsiklisheskikh soedinenii, Sbornik, 1971, 3, p. 108-111.
Fournie-Zaluski, M., Design of Orally Active dual Inhibitors of Neutral Endopeptidase and Angiotensin-converting Enzyme with Long Duration of Action, Journal of Medicinal Chemistry, 1996, 39(13), p. 2594-2608 Scheme.
Gershon, H. Amino Acid Anallogs. I. Analogs of the glutamic Acid-Proline Interconversion. III. Substituted 2—Acetamido-4-benzoylbutyric Acids and 5-Phenylprolines, Journal of Medicinal Chemistry, 1965, 8(6), p. 877-881.
Branchini, B.R., Naphtyyl- ad quinolylluciferin: greenand red light emitting firefly luciferin analogues, Photochemistry and Photobiology, 1989, 49(5), p. 689-695.
International Search Report from parent application—PCT/J2009/000376.
Office Action issued in Japanese Patent Application No. JP2008-023398, dated Sep. 9, 2013.
F. Kenya et al., "Synthesis and Emission of Light Activity of the Firefly Luciferin Analog (2)," the Chemical Society of Japan, the 87th spring annual convention, Mar. 12, 2007, p. 1245, 4 H4-31.

* cited by examiner

*Primary Examiner* — Bin Shen
(74) *Attorney, Agent, or Firm* — Edwards Wildman Palmer LLP; Nicholas J. DiCeglie, Jr.

(57) ABSTRACT

The present invention relates to a compound having a structure analogous to firefly luciferin. In particular, the invention relates to a heterocycle compound which produces a luminescence at a light wavelength different from that of firefly luciferin in nature. The present invention provides a heterocycle compound of following general formula I. In the above general formula, $R_1$, $R_2$ and $R_3$ can be each independently H or $C_{1-4}$-alkyl. In the above general formula, X and Y can be each independently C, N, S or O. In the above general formula, the olefin chain part expressed as "n" can be changed to desired length.

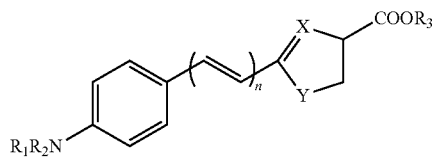

3 Claims, 2 Drawing Sheets

LUMINESCENT SUBSTRATE FOR LICIFERASE

RELATED APPLICATIONS

This application is a U.S. National Phase filing of PCT/JP2009/000376, filed on Feb. 2, 2009 which claims priority to Japanese patent application no. 2008-023396 filed on Feb. 2, 2008. The contents of each of these applications is incorporated herein by reference in their entirety.

FIELD OF THE INVENTION

The present invention relates to a compound having a structure analogous to firefly luciferin. In particular, the invention relates to a heterocycle compound which produces a luminescence at a light wavelength different from that of firefly luciferin in nature.

BACKGROUND ART

A Firefly Luciferin

The visualization of a biological event and the phenomena have been considered to be important, and it is desired that the object of visualization is expanded. Thus the diversification of a labeling technique is desired. In particular, the labeling technique for molecular imagings has been developed along with a progress of an apparatus for a diagnosis and examination. For example, the labeling techniques for applying to the advanced technology such as personalized medicines for cancer or cardiac disease are examined intensively. The needs for apparatuses and labeling materials with higher-sensitivity and higher-performance are also rapidly increasing, according to the measurement technology.

As is well known, the bioluminescent system of firefly shows great efficiency in luminescent, and it is said that this system is one of the most efficiently systems that can convert energy into a light. The understanding of the molecular mechanism of the bioluminescence is in advance.

It is known that this bioluminescence of the firefly emit a luminescence by chemically reacting with the luciferin which is luminescent substrate through the carton of the luciferase which is luminescent enzyme. In this reaction, the luminescent substrate is adenylated (luciferyl-AMP) in the presence of an adenosine triphosphate (ATP) and divalent magnesium ion ($Mg^{2+}$) lead to an adenylylated form which is substrate of an activated form. Then, a peroxide anion is produced by a luciferase of this form and converted into dioxetanone which is a high energy peroxide. The unstable dioxetanone dissolves itself and releases proton and carbon dioxide, and produce an excited singlet state of a monoanion form. Furthermore, this is protonated to produce an excited singlet state of a dianion form. It is assumed that the luminescence from the excited singlet state of a monoanion form is red. On the other hand, the luminescence from the excited singlet state of a dianion form is yellowish green, and this is assumed to be the luminescence of the firefly. The product after the luminescence is named oxyluciferin.

The luminescence of luciferin-luciferase reaction is very efficient and an elucidation of the molecular mechanism of the bioluminescence has been explained as described above. In light of these circumstances, the luminescent materials using the firefly bioluminescent system are commercially available from many companies. However, the research and development by the side of proteins (enzymes) have been done to a great extent, there are very few approaches from the side of a low molecular compound regarding to the luminescent materials relating to the firefly bioluminescence, because these materials have already been applied into practical use in the field of a medical and a biochemical field mainly. In particular, there are very few studies for correlation between a structure and an activity such as the structure of the luminescent substrate being converted.

Furthermore, the materials such as kit products, for labeling with luminescent using the firefly bioluminescent system are not inexpensive, although the luminescent enzyme can be provided at low cost by a recombination technique. This originates in that the luminescent substrate is the luciferin. The luciferin of D-form which is the luminescent substrate in nature is now synthesized by the D-cysteine which is not an amino acid of nature, which is one of the costly materials.

Needs and the Circumstance of the Luminescence of Multiple Colors Using the Bioluminescent System The luminescence of multiple colors is desired in a detection system using a label in order to observe many events. Therefore, it is desirable that a width of a wavelength of the labeling materials which is available for the detection system is broader. The labeling materials which is luminescent in red is desired for the use in a deep labeling in vivo in that the long wavelength light has greater optical transparency than the short wavelength light. For example, it is desirable that the label have the luminescent ranging from less than about 450 nm-more than about 650 nm in preparing the labeling materials.

There are substrates having some luminescent wavelengths which are available as the luminescent substrate for the firefly bioluminescent system. The both ends of the shortest and the longest wavelengths of these substrates are blue of a coelenterazine system (about 480 nm) and red of the firefly system (about 613 nm). They are available and manufactured from the Promega Inc. Also, the luminescent material of longer wavelength in red using the luminescent enzyme of the *Phrixothrix hirtus* is commercially available recently from TOYOBO Co., Ltd. The prospective potential needs are expected not only for these luminescent wavelengths, but also for the further expansion of the both ends of the shortest and the longest wavelengths in the luminescent wavelengths.

The example of the existing products having red and blue luminescence utilizing the bioluminescent system are shown in the followings:

1. Promega Inc.: Chroma-Luc: 613 nm (Non-patent literature 1)

This system utilizes a mutant of the Click Beetles and wild-type firefly luminescent substrate.

2. TOYOBO Co., Ltd.: MultiReporter Assay System-Tripluc: 630 nm (Non-patent literature 2)

This system utilizes the red luminescent enzyme of the railroad worm and wild-type firefly luminescent substrate. The luciferase gene of a green luminescent luciferase (SLG, maximum emission wavelength 550 nm), a orange luminescent luciferase (SLO, 580 nm) and a red luminescent luciferase (SLR, 630 nm) in the color was used to change the color of luminescent. Is it the utilization of the luminescent enzymes that bring different color of the luminescence.

3. University of Tokyo: Aminoluciferin: About 610 nm (patent document 1)

This discloses a luciferin derivatives.

4. Promega Inc.: Chroma-Luc: about 480 nm (Non-patent literature 3)

This system utilizes a coelenterazine and *Renilla reniformis* luciferase.

5. ATTO Inc.: *Vargula hilgendorfii* bioluminescence, about 460 nm (Non-patent literature 4)

This system utilizes a substrate of the coelenterazine system and *Renilla reniformis* luciferase.

We also disclose a compound analogous to luciferin in patent document 2. These compounds are compounds which have the structure analogous to luciferin.

patent document 1: Japanese Patent Application KOKAI Publication No. 2007-091695
patent document 2: International publication No. 2007/116,687
Non-patent literature 1: Promega Inc. general catalogue 2007, 12.16
Non-patent literature 2: Upload vol. 79, 2005 p 1-10, Toyobo Biochemicals for Lifescience 2006/2007 p 4-67
Non-patent literature 3: Promega Inc. general catalogue 2007, 12.14
Non-patent literature 4: ATTO Inc. general catalogue 2008-2009p 247

DISCLOSURE OF THE INVENTION

Problem to be Solved by the Invention

In view of the situation described above, the objective of the present invention can be stated as followings. First, it is to provide a substrate which produces the luminescence at a broad luminescent wavelength other than the wild-type firefly luminescent substrate. Second, to provide the substrate which can be synthesized at low cost. That is to say, the objective of the present invention is providing a substrate of firefly luminescent system which is more easily synthesized than the wild-type firefly luminescent substrate.

Means to Solve the Problem

For solving the above problems, as a result of enthusiastic studies, we found that the structure of the luciferin which is wild-type firefly luminescent substrate acted as luminescent substrate, when the structure is changed into simplified ones. We also found that the luminescent wavelength could be changed by making the luciferin of the phenol type in nature to that of the aniline type. Furthermore, we also found that the luminescent wavelength could be modified by changing the length of the olefin chain unit in the above simplified structures.

The present invention provides a heterocycle compound of following general formula I:

Wherein,
$R_1$, $R_2$ and $R_3$ are each independently H or $C_{1-4}$-alkyl, X and Y are each independently C, N, S or O, and n is 0, 1, 2 or 3.

The present invention also provides a heterocycle compound described above or the salt thereof, wherein $R_1$, $R_2$ and $R_3$ are each independently H or $C_{1-4}$-alkyl, X is N, Y is S, and n is 0, 1, 2 or 3.

Furthermore, the present invention provides a heterocycle compound described above or the salt thereof, wherein $R_1$ and $R_2$ are methyl respectively, $R_3$ is H, X is N, Y is S and, n is 0, 1, 2 or 3.

Furthermore, the present invention provides a heterocycle compound described above or the salt thereof, wherein n is 0, 1 or 2.

The present invention also provides a kit for detecting an luminescence comprising a compound described above with ATP and $Mg^{2+}$.

The present invention also provides a method for detecting an luminescence comprising: reacting a compound according to any one of claim 1-7 with luminescent beetle luciferase, and detecting an luminescence from the compound.

Effect of the Invention

The present invention provides the substrate which produce the luminescence at a broad luminescent wavelength other than the wild-type firefly luminescent substrate. The present invention also provides the substrate of firefly luminescent system which is more easily synthesized than the wild-type firefly luminescent substrate.

BEST MODE FOR CARRYING OUT THE INVENTION

The present invention provides a heterocycle compound of following general formula I:

In the above general formula, $R_1$, $R_2$ and $R_3$ can be each independently H or $C_{1-4}$-alkyl. Such lower alkyls as the substituent are not likely to have an influence on activity.

The term "$C_{1-4}$-alkyl" as used herein refers to an alkyl group of saturated, linear or brunched chain including 1-4 carbon atoms, for example methyl, ethyl, n-propyl, iso-propyl, n-butyl, iso-butyl, sec-butyl and tert-butyl. The term "$C_1$-$C_3$ alkyl" refers to an alkyl group of saturated, linear or brunched chain including 1-3 carbon atoms (for example, methyl, ethyl or iso-propyl).

It could be easily conceived by those skilled in the art that $R_3$ may be $C_{1-4}$-alkyl as discussed above. For example, the above patent document 2 by us shows the result that the compound analogous to luciferin in which the portion corresponding to the $R_3$ portion of the present invention can be the substrate of the firefly bioluminescent systems.

In the above general formula, each X and Y can be independently substitutable for C, N, S or O. It could be easily conceived by those skilled in the art that a heteroatom of X and Y may be C, N, S or O. For example, a various kinds of compounds analogous to luciferin described in the above patent document 2 by us shows the result that the compound analogous to luciferin in which the portion corresponding to the present invention is a various kinds of heteroatoms can be the substrate of the firefly bioluminescent systems.

In the above general formula, the olefin chain unit expressed as "n" can be changed to desired length. The luminescent wavelength could be modified by changing the length of the olefin chain portion. For example, in the case of n=0, the compound also has the luminescence of the blue at 445 nm which is shorter wavelength than the luciferin in nature. In the case of n=1, the compound also has the luminescence of the yellowish green luminescence at 565 nm which is roughly same wavelength as luciferin in nature. In the case of n=2, the compound also has the luminescence of the red at 680 nm which is longer wavelength than the luciferin in nature. Furthermore, in the case of n=more than 3, it is considered that the compound has the wavelength of the more than the infrared area which is longer wavelength than the wavelength of the luminescence of the red at 680 nm.

The term "the wavelength" as used herein regarding to the luminescent wavelength of the substrate mean the maximum wavelength thereof. For example, the luminescent spectrum (the left) obtained in a dimethyl aniline type luciferin shows the luminescent spectrum which has the largest wavelength at about 445 nm as described in FIG. 1, and it is expressed as simply "it has the luminescence at 445 nm" in the present specification.

The compound of general formula I has the largely simplified structure compared to the luciferin which is wild-type firefly luminescent substrate as described above.

In one embodiment, a compound of the present invention is a heterocycle compound of following general formula II dimethyl aniline-diene type luciferin This compound has the wavelength that is longer than the infrared area which is longer wavelength than that of the luminescence of the red at 680 nm.

In one embodiment, a compound of the present invention is a heterocycle compound of following general formula III dimethyl aniline-monoene type luciferin This compound has the luminescence of the yellowish green luminescence at 565 nm which is roughly same wavelength as luciferin in nature.

In one embodiment, a compound of the present invention is a heterocycle compound of following general formula IV dimethyl aniline type luciferin This compound the luminescence of the blue at 445 nm which is shorter wavelength than the luciferin in nature.

The compounds of the above present invention include the salt thereof. The "salt", in the compound of the present invention, is made, only when the compound can form a base.

The expression "salt" includes an organic acid and an inorganic acid such as a hydrochloric acid, a hydrobromic acid, an iodinated hydracid, sulfuric acid, sulfamic acid, phosphoric acid, nitric acid, phosphoric acid, nitrous acid, citric acid, a formic acid, acetic acid, oxalic acid, maleic acid, lactic acid, tartaric acid, fumaric acid, benzoic acid, Mandel acid, cinnamic acid, pamoic acid, stearic acid, glutaminic acid, aspartic acid, methane sulfonic acid, ethane disulfonic acid, p-toluene sulfonic acid, salicylic acid, succinic acid, trifluoroacetic acid and others that are non-toxic for a living organism, or salt with a inorganic base such as alkali or an alkaline earth base, for example sodium hydroxide, a potassium hydroxide, calcium hydroxide and the like, when the property of the compound of formula I is acid.

The compound of the present invention can be made according to the procedure described below in the example 1. More detailed procedures are described in the examples below. The compound of the dimethyl aniline type wherein $R_1$ and $R_2$ of general formula I are methyl respectively, $R_3$ is H, and n is 2 is described in the example 1. Briefly, using commercially available 4-(dimethylamino)cinnamicaldehyde as a starting material, it is reacted with a carbetoxymethylenetriphenylphospholan to give an ethyl ester form. Then this ethyl ester form is converted into a carboxyl form in a solution of a sodium hydroxide in water. On the other hand, a D-cysteine-S-trityl compound is reacted in solution of a hydrogen chloride and a 1,4-dioxane, and produced a methyl ester form. Then this methyl ester form is reacted with the carboxyl form and produces an amide form. Then this amide form is cyclized with triphenyl phosphine oxide and trifluoromethane sulfone acid anhydride to generate a heterocycle to give a thiazoline form. Then the methyl ester moiety of the thiazoline form is converted into a desired substituent to give a desired compound.

It will be understandable that those skilled in the art that commencing from the starting material wherein $R_1$ and $R_2$ is replaced with a desired substituent, the corresponding compounds can be synthesized by reaction with the methyl ester form derived from a D-cysteine-S-trityl according to the procedure same as the example 1. In the final procedure, a compound having a corresponding $R_3$ may be obtained by replacing the methyl ester moiety of the thiazoline form with desired ester. Furthermore, the compound which has desired n in length in general formula I may be obtained by changing the length of the olefin moiety in the ethyl ester form used as starting material.

The compound of the present invention produce luminescent by being oxidized with luminescent beetle luciferase by adding to the system presenting luminescent beetle luciferase, ATP and $Mg^{2+}$ to produce the luminescent. The compound of the present invention can be used as luminescent substrate alone, but it may be used in combination with other luminescent substrate if necessary. The compound of the present invention can be provided as a kit with ATP and $Mg^{2+}$. The kit can include the luminescent substrate and a solution which was prepared in an appropriate pH. Furthermore, the compound of the present invention can be provided as a composition of the luminescent substrate which was prepared in an appropriate pH in kit with ATP and $Mg^{2+}$.

The firefly bioluminescent system is aqueous system and there may be a hydrophilic organic compound. For example, There may be tetrafluoroacetic acid, acetic acid and a formic acid. When the compound of the present invention is applied to the luminescent system, preferred, for example, it is preferable to use it at a concentration of more than 1 μM of the luminescent substrate in order to obtain preferred luminescence strength, for example it is used at more than 5 μM. It is also contemplated, but not limited to, that the pH of the luminescent system is 4-10, preferably 6-8. Buffers such as potassium phosphate, tris hydrochloric acid, glycine and HEPES can be used to make pH stabilize if necessary.

The compound of the present invention also can produce the luminescentin firefly luminescent beetle luciferase luminescent system by various kinds of oxidizing enzymes. The luciferase is isolated by the various kinds of creatures such as firefly from North America (*Photinus pyralis*) and Railroad worm, which can be used. For example, the oxidizing enzymes which can be used include *Pyrearinus termitilluminans* luciferase, *Rhagophthalmus ohbai* luciferase and flavin containing monooxygenases.

The bioluminescence which use the compound of the present invention as the luminescent substrate is known to be able to enhanced when a coenzyme A (CoA), pyrophosphoric acid or a magnesium ion ($Mg^{2+}$) in the luminescent system. Therefore, they can be used as an enhancer of the luminescent in the luminescent beetle luciferase luminescent system. The enhancing effect of these compounds remarkable when the concentration of the CoA, the pyrophosphoric acid or the $Mg^{2+}$ in the luminescent system is more than 5 μM respectively, it is known to be enhanced according to increase of the concentration.

It is important to make stabilize the luminescence such that the deactivation of the enzyme is prevented and the luminescent behavior that is a plateau is show in order to use the firefly bioluminescent system for the measurement/detection. For example, a Mg ion is effective for the stabilization of the luminescence in the firefly bioluminescent system. When Mg ion exist in the luminescent system, the luminescent behavior changes such as showing suppression of decrement after being risen. In particular, when a pyrophosphoric acid and a Mg ion co-exist in the luminescent system, the luminescent behavior changes greatly. In other words, the stabilization of the luminescence is very remarkable, and the luminescent behavior will be risen up rapidly and the condition is maintained to produce the plateau state, when the pyrophosphoric acid and the Mg ion co-exist in excess compared to the luminescent substrate. When the Mg ion exists alone, the effect of the luminescent stabilization is remarkable in a concentration of more than 0.5 mM of Mg ion in the luminescent system and it is enhanced according to increase of the concentration. For example, the concentration of more than 10 μM, preferably more than 100 μM of magnesium pyrophosphate can be existed in order to achieve the plateau behavior of the luminescence. The ratio of the pyrophosphoric acid to the Mg ion also does not need to be equivalent ratio. Although the magnesium pyrophosphate has low solubility, the pyrophosphoric acid and the Mg ion can be provided separately by using this. They can be supplied in the luminescent system in the form of a salt and free form. The available Mg salt includes salts of an inorganic acid such as a magnesium sulfate and the magnesium chloride and salts of organic acid such as magnesium acetate. The pyrophosphate includes salts with alkali metals such as sodium and the potassium and salts with alkaline-earth metals such as magnesium and the calcium, and salt with iron and the like. They may include in the form of solution in the luminescent system. It is preferable that the pH of the luminescent system become 2-10 in consideration of the influence on enzyme, what can be included to become is desirable for the pH pro-luminescence.

The compound of the present invention may be used as a substrate in the chemiluminescence. The chemiluminescence occurs by oxidizing the compound of the present invention to produce a peroxide, and producing the luminescence class of the excited state by degradation of this peroxide. The oxidation can be progressed by oxidation in air, for example in DMSO using potassium t-butoxide. In the case of chemiluminescence, the luminescence is considered to be shorter wavelength than the luminescence of the firefly bioluminescent system.

The compound of the present invention can be used as a luminescence label in the biological measurement/detection. For example, it can be used to label an amino acid, a polypeptide, a protein and a nucleic acid. The means to conjugate the compound of the present invention to these materials is well-known to those skilled in the art. For example, the compound of the present invention can be conjugated to a carboxyl group and an amino group of the objective material using a method well known to those skilled in the art.

The compound of the present invention can be utilized in the measurement/detection using a detection of the luminescent beetle luciferase activity by the luminescence of the luminescent substrate. For example, the compound of the present invention is reacted with the luminescent beetle luciferase such as described above under a condition suitable for reaction. Then the luminescence from said compound is detected. For example, an in vivo expression of a target gene and protein can be measured/detected by administering the compound of the present invention to the cell or the animal which was introduced the luciferase gene. The compound of the present invention can produce the different luminescent wavelength respectively. Therefore, the luminescence from plural targets can be measured/detected by using plural compounds. The longer the wavelength, the higher optical transparency, and a permeability of the organization is also higher. Therefore, among the compounds of the present invention, the compound of the long wavelength is useful for a in vivo labeling of deep part.

The present invention can achieve the blue luminescence at 445 nm and the yellow green luminescence at 565 nm roughly same as natural form, and furthermore the red luminescence at 680 nm. The luminescence of RGB which is three primary colors of the light can be achieved with firefly luciferin analogs according to these a series of these analogs of the substrate. The blue which is a short wavelength than 450 nm and the red which is a long wavelength than 650 nm at the both ends are the luminescent wavelength region where the existing firefly bioluminescent system has not been able to be achieved.

The luminescences by the compound of the present invention correspond to RGB which is three primary colors of the light as described above. It is well known that any color can be given by combining three primary colors of the light. Therefore, the luminescence of an infinite color can be given by combining the compound of the luminescent wavelength corresponding to three primary colors. If the compounds of the luminescent wavelength corresponding to three primary colors are utilized for the measurement/detection using detection of the luminescent beetle luciferase activity by the luminescence of the luminescent substrate, then the luminescence of the color depending to the degree of each luminescence of three primary colors will be provided. Therefore, the degree of each luminescence of three primary colors may be judged at the same time from the color of the provided luminescence. A desired wavelength can be sorted, and measured and detected using filters.

The luminescent substrate which produces the luminescence at a shorter wavelength (less than about 500 nm) than the firefly luciferin can transfer the energy to green fluorescence protein (GFP) of luminescent *Aequorea victoria*. The fluorescence (about 520 nm) is emitted from green GFP by such an energy transfer. The luminescent system of the BRET (Bioluminescence Resonance Energy Transfer) type can be constituted by the GFP/luminescent beetle luciferase fusion protein using this luminescent substrate. By the BRET type luminescent system, the bioimaging of a post-translational modification of various kinds of proteins and the gene expression is enabled. For example, when the GFP and the luminescent beetle luciferase fusion protein is expressed thorough a protein processing sequence, the green fluorescence of GFP is detected where the fusion protein has not been processed. On the contrary, the blue luminescence of the luminescent substrate is detected upon processing a fusion protein. Therefore, the bioimaging regarding to the expression of the enzyme which process the fusion protein is enabled based on a luminescence state. The measurement of the quantity of protein and the bioimaging of the localization of the protein is enabled. Furthermore, it can be utilized to the bioimaging of the process of glycosylation which is necessary for maturation of the protein. It can be utilized to observe interaction between the protein/protein.

EXAMPLES

The present invention will be described in more detail in the following examples, however, the present invention is not limited to these ranges.

1) Instrumental Analysis and a Measuring Device pH measurement: They were measured using pH test paper UNIV which was made by Toyo Roshi Kaisha, Ltd. It was also measured using pH/ION METERF-23 made from Horiba Corporation as a pH meter.

Measurement of a melting point (m.p.): It is measured using model MP-2 made in Yamamoto Ltd. The measurements are not calibrated.

Infrared absorption spectrum (IR): They were measured by a tablet method (KBr), a solution method ($CHCl_3$, $CH_3OH$) using a FT-730 Fourier transform infrared spectrophotometer made by Horiba, Ltd. The measurements are described in a wavenumber ($cm^{-1}$). Note that the broad absorption was written as br.

$^1H$ nuclear magnetic resonance spectrum (1H NMR): They were measured using a Lambda-270 type device (270 MHz) made by JEOL, Ltd. It was described as "$^1H$ NMR (measured frequency, measured solvent): δ chemical shift value (the number of hydrogen, multiplicity, spin binding constant)". The chemical shift value (δ) is expressed as ppm using a tetramethylsilane (δ=0) as an internal standard. The multiplicity is expressed as s (single), d (doublet), t (triplet), q (quadruplet), m (multiplet or a multiple signal), and the broad signal is described in br. The spin binding constant (J) is described in Hz.

$^{13}C$ nuclear magnetic resonance spectrum (13C NMR): They were measured using a Lambda-270 type device (67.8 MHz) made from Horiba, Ltd. It was described as "$^{13}C$ NMR (measured frequency, measured solvent): δ chemical shift value (multiplicity)". The chemical shift value (δ) is expressed as ppm using a tetramethylsilane (δ=0) as an internal standard. The multiplicity is expressed as s (single), d (doublet), t (triplet), and q (quadruplet).

Mass spectrum (MS): They were measured using JMS-600H type mass spectrometer made from JEOL, Ltd. by an electron ionization mass spectrometry (EI, ionization energy: 70 eV). They were measured using JMS-T100LC type TOF mass spectrometer AccuTOF made by JEOL, Ltd. by electrospray ionization mass spectrometry (ESI). Note that the settings of the device was desolvent gas 250 degrees Celsius, temperature of orifice 1 80 degrees Celsius, needle voltage 2,000V, ring lens voltage 10V, voltage of orifice 1 85V, voltage of orifice 2 5V. The delivery of samples in solution is made by infusion method with flow speed 100/min. They were described as "Nuclear number MS (method for measurement) m/z" (relative strength).

Relative optical rotation: They were measured using DIP-1000 type azimuthal polarimeter made in JASCO Corporation. The sodium lamp was used as a light source, the cylinder type glass cell (Φ10×100 mm) was used as a cell. The measurements are not calibrated, and the data is the means of the measurement of five times. They are described as "D or L: $[\alpha]^{temperature}$ measurements (concentration, measured solvent)" regarding to D form and an L form respectively.

2) Chromatography

Analytical thin layer chromatography (TLC): TLC plate made in E.Merck KG, Silicagel 60F254 (Art. 5715), thickness 0.25 mm were used. The compound on TLC was detected by heating and development after UV irradiation (254 nm or 365 nm) and dipped in a color coupler. A p-anisic aldehyde (9.3 ml) and an acetic acid (3.8 ml) are dissolved in ethanol (340 ml) and added conc. sulfuric acid (12.5 ml) and used as the color coupler.

Preparative thin layer chromatography (PTLC): TLC plate made from E.Merck KG, Silicagel 60F254 (Art. 5744), thickness 0.5 mm were used or Silicagel 60GF254 (Art. 7730) for thin layer chromatography manufactured by E.Merck KG is prepared on the glass plate of 20 cm×20 cm at 1.75 mm of thickness and use it.

Silica gel column chromatography: Silicagel 60F254 (Art. 7734) made from E.Merck KG was used.

3) Elementary Operation

The reaction solution was cooled by soaking the reaction vessel into Dewar flask filled with a refrigerant. An iced water was used as refrigerant at room temperature to 4 degrees Celsius, and a liquid nitrogen-acetone was used at 4 to minus 90 degrees Celsius. The extracted solution after the reaction was dried by adding solution such as a sodium sulfate anhydrite or a magnesium sulfate anhydrite after washing with a saturated saline. To neutralize by the resin after the reaction, the amberite IR120B NA of a cation exchange resin or the amberite IRA400 OH AG of an anion exchange resin made from ORGANO CORPORATIO was used. The vacuum concentration of the solution was performed using a rotary evaporator under reduced pressure (20-30 mmHg) in the aspirator. The solvent of the amount of trace was removed by using a vacuum pump (about 1 mmHg) equipped with a trap which was cooled off in a liquid nitrogen bath. The ratio of mixture of each solvent were all expressed by a ratio of volume.

4) Solvents

The distilled water has been made by distilled and treated by ion exchange using the GS-200 type distilled water manufacturing apparatus manufactured by ADVANTEC MFS, INC. and use it.

Toluene, methanol, ethanol, isopropanol, dichloromethane, tetrahydrofuran, a N,N-dimethylformamide, and 2-butanone was used by drying a dehydration solvent for organic synthesis or a reagent solvent made from Kanto Chemical Co., Ltd using Molecular sieve (4 A).

The solvents shown in the followings were used for NMR measurement. $CDCl_3$: made by ISOTEC Inc. 99.7 ATOM %

D, 0.03% TMS, CD$_3$OD: made by ISOTEC Inc. 99.8 ATOM % D (~0.7 ATOM % $^{13}$C), 0.05% TMS.

Example 1-1

Synthesis of the Ethyl Ester Form 4-dimethyl cinnamyl aldehyde (104 mg, 0.592 mmol) was dissolved in toluene (9 ml) and Carbethoxy methylene triphenyl phospholan (621.6 mg, 1.78 mmol) was added and heated to reflux in 4.5 hours. After cooling of the reaction mixture in air, water (50 ml) was added and extracted in ethyl acetate (3×50 ml), and the organic layer was dried over sodium sulfate anhydrite, thereafter concentrated in vacuum. The obtained residue was purified by silica gel column chromatography {Silicagel 192 g, Hexane-ethyl acetate (3:2)}, to give ethyl ester form (144 mg, 99%) as a yellow solid.

Example 1-2

Synthesis of the Carboxyl Form

The above ethyl ester form (235 mg, 1.08 mmol) was dissolved in isopropyl alcohol (7 ml) and 1 M sodium hydroxide in water (4 ml, 4 mmol) was added. After stirred at room temperature for 3 days, it was neutralized using 1 M hydrochloric acid. Water (50 ml) was added to it and extracted in ethyl acetate (3×50 ml), and the organic layer was dried over sodium sulfate anhydrite, thereafter concentrated in vacuum to gibe a carboxyl form (137.1 mg, 58%) as a yellow solid.

Example 1-3

Synthesis of the Methyl Ester 1

D-cysteine-S— bird till compound (497 mg, 1.37 mmol) was dissolved in methanol (60 ml), and 4N of solution of hydrogen chloride in 1,4-dioxane (4 ml) was added. After stirred at room temperature for 18 days, it was neutralized using anion exchange resin IRA400 OH AG. Resin is filtered, the obtained solution was concentrated in vacuum. The residue was purified by silica gel column chromatography {Silicagel 44.0 g, hexane-ethyl acetate (2:3)} to give a methyl ester 1 (421 mg, 81%) as pale yellow oil.

Methyl Ester 1

IR (neat) 3381, 3317, 1739, 1595 cm$^{-1}$ $^1$H NMR (270 MHz, CD$_3$OD): δ 2.46 (1H, dd, J=7.1, 12.4 Hz), 2.58 (1H, dd, J=5.8, 12.4 Hz), 3.11 (1H, dd, J=5.8, 7.1 Hz), 3.65 (3H, s), 7.19-7.32 (9H, complex), 7.32-7.42 (6H, complex)

$^{13}$C NMR (67.8 MHz, CD$_3$OD): δ 37.37 (t), 52.62 (q), 54.42 (d), 67.86 (s), 127.87 (d), 128.97 (d), 130.64 (d), 145.82 (s), 174.98 (s).

Example 1-4

Synthesis of the Amide Form

To the solution of methyl ester form 1 (147 mg, 0.387 mmol) in N,N-dimethylformamide (4 ml), the carboxyl form (81.4 mg, 0.375 mmol), 1-ethyl-3-(3-dimethylamino propyl) carbodiimide hydrochloride (181 mg, 0.944 mmol), and 4-dimethyl aminopyridine (103 mg, 0.845 mmol) are added under argon atmosphere, and stirred at room temperature for 18 hours. Water (100 ml) was added to the reaction mixture and extracted in a diethyl ether (3×100 ml), and the organic layer was dried over sodium sulfate anhydrite, thereafter concentrated in vacuum. The obtained residue was purified by silica gel column chromatography {Silicagel 112 g, hexane-ethyl acetate (3:2)} to give amide form (158 mg, 73%) as yellow oil.

Example 1-5

Synthesis of the Thiazoline Form

To the solution of the amide form (43.3 mg, 0.0751 mmol) in the dichloromethane (5 ml), Triphenyl phosphine oxide (44.9 mg, 0.161 mmol), trifluoromethanesulfonate anhydride (17 μl, 0.101 mmol) are added under argon atmosphere and stirred at room temperature for 80 minutes. Water (50 ml) is added to the reaction mixture and extracted in chloroform (50 ml) and ethyl acetate (2×50 ml), and the organic layer was dried over sodium sulfate anhydrite, thereafter concentrated in vacuum. The obtained residue was purified by silica gel column chromatography {20 cm×20 cm×0.5 mm 3×; hexane-ethyl acetate (1:1)} to give the thiazoline form (17.6 mg, 74%) as a pale yellow solid.

Thiazoline of the Dimethylamino Diene
$^1$H NMR (270 MHz, CDCl$_3$)
δ 3.00 (6H, s), 3.54 (1H, dd, J=8.9, 11 Hz), 3.57 (1H, dd, J=8.9, 11 Hz), 5.17 (1H, t, J=8.9 Hz), 6.54 (1H, d, J=15 Hz), 6.65-6.80 (4H, complex), 6.94 (1H, dd, J=8.9, 15 Hz) 7.36 (2H, d, J=8.9 Hz).

Example 1-6

Synthesis of the Diene Form of the Luminescent Substrate

The thiazoline form (12.7 mg, 0.0402 mmol) was dissolve in the mixed solution of ethanol (2 ml) and 10 mM ammoniumbicarbonate in water (6 ml) and a small amount of an esterase of a pig liver was added under argon atmosphere. After stirred at 36 degrees Celsius for 25 hours, the reaction mixture is filtered and the solution was concentrated in vacuum to give the analog (10.2 mg, quant.) as pale yellow solid.

Dimethylamino Diene Form of the Luminescent Substrate
$^1$H NMR (270 MHz, CD$_3$OD)
δ 2.98 (6H, s), 3.54 (1H, d, J=8.9 Hz), 3.57 (1H, d, J=8.9 Hz), 5.19 (1H, t, J=8.9 Hz), 6.47 (1H, d, J=15 Hz), 6.70-7.06 (5H, complex), 7.38 (2H, d, J=8.9 Hz).

Example 2-1

Synthesis of the Amide Form

To the solution of methyl ester form 1 (184 mg, 0.485 mmol) in N,N-dimethylformamide (5 ml), p-dimethylamino cinnamic acid (92.1 mg, 0.482 mmol), 1-ethyl-3-(3-dimethylamino propyl) carbodiimide hydrochloride (196 mg, 1.02 mmol), 4-dimethyl aminopyridine (124 mg, 1.02 mmol) were added under argon atmosphere, and stirred at room temperature for four hours. Water (100 ml) was added to the reaction mixture and extracted in ethyl acetate (3×100 ml), and the organic layer was dried over sodium sulfate anhydrite, thereafter concentrated in vacuum. The obtained residue was purified by silica gel column chromatography {Silicagel 181 g, hexane-ethyl acetate (1:1)} to give the amide form (214 mg, 80%) as yellow oil.

Amide of Dimethylaminomonoen
$^1$H NMR (270 MHz, CDCl$_3$)
δ 2.99 (6H, s), 3.71 (3H, s), 4.78 (1H, dd, J=5.1, 7.8 Hz), 6.05 (1H, d, J=7.8 Hz), 6.15 (1H, d, J=15 Hz), 6.66 (1H, d, J=8.6 Hz), 7.16-7.40 (19H, complex), 7.53 (1H, d, J=15 Hz).

Example 2-2

Synthesis of the Thiazoline Form

To the solution of the amide form (118 mg, 0.214 mmol) in the dichloromethane (10 ml), triphenyl phosphine oxide (124 mg, 0.446 mmol), trifluoromethane sulfone acid anhydride (360 μl, 2.14 mmol) are added under argon atmosphere and stirred at room temperature for 40 minutes. Water (50 ml) was added to the reaction mixture and extracted in chloroform (50 ml), ethyl acetate (2×50 ml), and the organic layer was dried over sodium sulfate anhydrite, thereafter concentrated in vacuum. The obtained residue was purified by silica gel column chromatography {Silicagel 42 g, hexane-ethyl acetate (1:2)} to give the thiazoline form (44.2 mg, 71%) as yellow solid.

Thiazoline Form of Dimethylaminomonoen $^1$H NMR (270 MHz, CDCl$_3$)

δ 3.00 (6H, s), 3.56 (1H, dd, J=9.2, 11 Hz), 3.58 (1H, dd, J=9.2, 11 Hz), 3.83 (3H, s), 5.18 (1H, t, J=9.2 Hz), 6.67 (2H, d, J=9.5 Hz), 6.91 (1H, d, J=16 Hz), 7.07 (1H, d, J=16 Hz), 7.38 (2H, d, J=9.5 Hz).

Example 2-3

Synthesis of the Monoene Form of the Luminescent Substrate

The thiazoline form (16.3 mg, 0.0591 mmol) was dissolved in the mixed solution of ethanol (2 ml) and 10 mM ammoniumbicarbonate in water (8 ml) and a small amount of an esterase of a pig liver was added under argon atmosphere. After stirred at 36 degrees Celsius for 19 hours, the reaction mixture is filtered and the solution was concentrated in vacuum to give the analog (15.2 mg, quant.) as orange solid.

Monoene Form of the Luminescent Substrate

$^1$H NMR (270 MHz, CD$_3$OD)

δ 3.02 (6H, s), 3.57 (1H, dd, J=8.6, 11 Hz), 3.72 (1H, dd, J=8.6, 11 Hz), 5.03 (1H, t, J=8.6 Hz), 6.73 (2H, d, J=8.9 Hz), 6.87 (1H, d, J=16 Hz), 7.24 (1H, d, J=16 Hz), 7.45 (2H, d, J=8.9 Hz).

Example 3

Synthesis of the Dimethyl Aniline Form of the Luminescent Substrate 4-dimethyl amino benzonitrile (103 mg, 0.706 mmol) and D-cysteine hydrochloride monohydrate (371 mg, 2.12 mmol) was dissolved in ethanol (4 ml) and 1M sodium hydroxide in water (5 ml) was added under argon atmosphere and stirred at 80 degrees Celsius for 5 hours. After 1 M hydrochloric acid (5 ml) was added to the reaction mixture to make it acidic, and concentrated in vacuum. The obtained solid was filtered and washed with distilled water to give analogs (50.9 mg, quant.) as yellow solid.

Dimethyl Aniline Form of the Luminescent Substrate $^1$H NMR (270 MHz, CDCl$_3$)

δ 3.01 (6H, s), 3.50 (1H, dd, J=9.2, 11 Hz), 3.61 (1H, dd, J=9.2, 11 Hz), 5.00 (1H, t, J=9.2 Hz), 6.71 (2H, dd, J=2.4, 7.0 Hz), 7.71 (2H, dd, J=2.4, 7.0 Hz).

Example 4-1

Deprotection of the Methyl (Synthesis of the Phenol Form 13)

To the commercially available 2-ciano-6-methoxy benzothiazole (651.7 mg, 3.43 mmol), pyridinium chloride (30.6 g, 265 mmol) was added and heated to 20 degrees Celsius in argon atmosphere, and melted pyridinium chloride and stirred for 30 minutes. After cooling of the reaction mixture in air, 1 M hydrochloric acid (80 ml) was added and extracted in ethyl acetate (4×60 ml). The organic layer was dried over sodium sulfate anhydrite, thereafter concentrated in vacuum. The obtained residue was purified by silica gel column chromatography {Silicagel 85 g, chloroform-methanol (10:1)} to give the phenol form 13 (448.8 mg, 74%) as a yellow solid. Raw materials (213.4 g, 1.12 mmol) were also collected.

Phenol Form 13 mp 155-170° C. decomp.

IR (film) 3178, 2225 cm$^{-1}$

$^1$H NMR (270 MHz, CD$_3$OD): δ 7.17 (1H, dd, J=2.6, 8.9 Hz), 7.40 (1H, d, J=2.6 Hz), 7.99 (1H, d, J=8.9 Hz)

$^{13}$C NMR (67.8 MHz, CD$_3$OD): δ 107.00 (d), 114.29 (s), 119.61 (d), 126.58 (d), 133.91 (s), 139.01 (s), 147.29 (s), 160.32 (s)

MS (EI) m/z 176 (M$^+$., 100), 124 (5).

Example 4-2

Synthesis of the Firefly Luciferin (1)

The phenol form 13 (20.0 mg, 0.114 mmol), D-cysteine hydrochloride monohydrate (19.7 mg, 0.125 mmol) was dissolvesed in methanol:distilled water (2:1) (3.0 ml), and potassium carbonate (17.0 mg, 0.123 mmol) was added under argon atmosphere and stirred at room temperature for 30 minutes. 0.2 ml of 1M hydrochloric acid was added to the reaction mixture to make it acidic, thereafter concentrated in vacuum. The obtained solid was filtered and washed with distilled water to give the firefly luciferin (1) (23.5 mg, 74%) as yellow solid.

A Firefly Luciferin (1)

$^1$H NMR (270 MHz, DMSO-$d_6$): δ 3.66 (1H, dd, J=8.2, 11.2 Hz), 3.67 (1H, dd, J=9.9, 11.2 Hz), 5.40 (1H, dd, J=8.2, 9.9 Hz), 7.06 (1H, dd, J=2.6, 8.9 Hz), 7.51 (1H, d, J=2.6 Hz), 7.96 (1H, d, J=8.9 Hz), 10.24 (1H, br.s, OH)

$^{13}$C NMR (67.8 MHz, DMSO-$d_6$): δ 34.5 (t), 78.0 (d), 106.7 (d), 117.0 (d), 124.8 (d), 137.1 (s), 146.1 (s), 157.3 (s), 159.8 (s), 164.3 (s), 171.1 (s).

Example 4-3

Synthesis of the Analogs 7 p-cyanophenol (229.6 mg, 1.93 mmol) and D-cysteine hydrochloride monohydrate (1.73 g, 9.82 mmol) were dissolved in the mixed solution of the degassed ethanol (5.0 ml) and 1M sodium hydroxide in water (15.0 ml) under argon atmosphere and heated and stirred at 80 degrees Celsius for 18 hours. After cooling of the reaction mixture in air, water (80 ml) was added and extracted in ethyl acetate (3×130 ml). The organic layer was dried over sodium sulfate anhydrite, thereafter concentrated in vacuum to give the analogs (388.2 mg, 90%) as colorless solid.

Analogs 7 mp 200-204° C. decomp.

IR (film) 3066, 1652, 1583 cm$^{-1}$ $^1$H NMR (270 MHz, CD$_3$OD): δ 3.70 (1H, dd, J=7.9, 11.5 Hz), 3.76 (1H, dd, J=8.9, 11.5 Hz), 5.23 (1H, dd, J=7.9, 8.9 Hz), 6.85 (2H, d, J=8.9 Hz), 7.74 (2H, d, J=8.9 Hz)

$^{13}$C NMR (67.8 MHz, CD$_3$OD): δ 35.95 (t), 77.97 (d), 116.53 (d)×2, 124.48 (s), 131.80 (d)×2, 163.00 (s), 173.94 (s), 174.63 (s)

MS (EI) m/z 223 (M$^+$., 44), 178 (100), 137 (43), 119 (46)

Optical rotation: L: [α]$^{25}$ −1.0600° (c=1.2000, CH$_3$OH), D: [α]$^{22}$ +6.6979° (c=0.7692, CH$_3$OH).

Example 5-1

Synthesis of the Ester Form 15

D-cysteine-S-trityl compound (932.8 mg, 2.57 mmol) was dissolved methanol (200 ml) and the solution of 4N of hydrogen chloride in 1,4-dioxane (10 ml, 40 mmol) was added. After stirred at room temperature for two days, it was neutralized using anion exchange resin IRA400 OH AG. The resin was filtered and the obtained solution was concentrated in vacuum. The obtained residue was purified by silica gel column chromatography {Silicagel 85 g, hexane-ethyl acetate (2:01)→chloroform-methanol (10:1)}, to give the ester form 15 (414.6 mg, 43%) as pale yellow oil.

Ester Form 15

IR (neat) 3381, 3315, 1739, 1595 cm$^{-1}$

$^1$H NMR (270 MHz, CDCl$_3$): δ 2.47 (1H, dd, J=7.7, 12.4 Hz), 2.60 (1H, dd, J=4.8, 12.4 Hz), 3.20 (1H, br.dd, J=4.8, 7.7 Hz), 3.65 (3H, s), 7.18-7.31 (9H, complex), 7.40-7.45 (6H, complex)

$^{13}$C NMR (67.8 MHz, CDCl$_3$): δ 36.90 (t), 52.16 (q), 53.78 (d), 66.83 (s), 126.76 (d)×3, 127.94 (d)×6, 129.57 (d)×6, 144.51 (s)×3, 174.18 (s)

MS (FAB) m/z 378 (M+H$^+$, 10), 243 (100).

Example 5-2

Synthesis of the Acetyl Form 16

To the solution of the p-hydroxy cinnamic acid (254.2 mg, 1.55 mmol) in dichloromethane (20 ml), acetic anhydride (0.5 ml, 5.3 mmol) and 4-dimethyl aminopyridine (572.0 mg, 4.68 mmol) were added. After stirred at room temperature for four hours, 1M hydrochloric acid (40 ml) was added to the reaction mixture and extracted in dichloromethane (1×50 ml) and ethyl acetate (2×50 ml). The organic layer was dried over sodium sulfate anhydrite, thereafter concentrated in vacuum. The residue was purified by silica gel column chromatography {Silicagel 200 g, hexane-ethyl acetate (2:1)} to give the acetyl form 16 (303.4 mg, 95%) as colorless crystal.

Acetyl Form 16 mp 182-183° C.

IR (film) 3050, 1743, 1680, 1630 cm$^{-1}$ $^1$H NMR (270 MHz, CDCl$_3$): δ 2.33 (3H, s), 6.41 (1H, d, J=16.0 Hz), 7.15 (2H, d, J=8.7 Hz), 7.58 (2H, d, J=8.7 Hz), 7.77 (1H, d, J=16.0 Hz)

$^1$H NMR (270 MHz, CD$_3$OD): δ 2.28 (3H, s), 6.47 (1H, d, J=16.0 Hz), 7.14 (2H, d, J=8.6 Hz), 7.58-7.64 (3H, complex)

$^{13}$C NMR (67.8 MHz, CD$_3$OD): δ 20.95 (q), 120.99 (d), 123.37 (d)×2, 130.20 (d)×2, 133.86 (s), 144.18 (d), 153.60 (s), 170.85 (s), 171.23 (s)

MS (EI) m/z 206 (M$^+$., 14), 164 (100), 147 (20), 119 (12), 92 (14).

Example 5-3

Synthesis of the Amide Form 17

To the solution of ester form 15 (164.0 mg, 0.435 mmol) in N,N-dimethylformamide (80 ml), acetyl form 16 (109.4 mg, 0.531 mmol), 1-ethyl-3-(3-dimethylamino propyl) carbodiimide hydrochloride (252.6 mg, 1.32 mmol) and 4-dimethylaminopyridine (166.4 mg, 1.36 mmol) ware added under argon atmosphere and stirred at room temperature for four hours. Water (100 ml) was added to the reaction mixture and extracted in a diethyl ether (3×180 ml). The organic layer was dried over sodium sulfate anhydrite, thereafter concentrated in vacuum. The residue was purified by silica gel column chromatography {Silicagel 245 g, hexane-ethyl acetate (2:1)} to give the amide form 17 (111.4 mg, 37%) as pale yellow oil.

Amide Form 17

IR (neat) 3282, 1763, 1743, 1662, 1626 cm$^{-1}$ $^1$H NMR (270 MHz, CDCl$_3$): δ 2.32 (3H, s), 2.70 (1H, dd, J=4.8, 12.4 Hz), 2.78 (1H, dd, J=5.4, 12.4 Hz), 3.74 (3H, s), 4.58 (1H, ddd, J=4.8, 5.4, 7.7 Hz), 6.10 (1H, d, J=7.7 Hz), 6.30 (1H, d, J=15.7 Hz), 7.12 (2H, d, J=8.6 Hz), 7.18-7.31 (9H, complex), 7.37-7.41 (6H, complex), 7.52 (2H, d, J=8.6 Hz), 7.57 (1H, d, J=15.7 Hz)

$^{13}$C NMR (67.8 MHz, CDCl$_3$): δ 21.16 (q), 33.94 (t), 51.20 (d), 52.74 (q), 67.00 (s), 120.04 (d), 122.09 (d)×2, 126.94 (d)×3, 128.04 (d)×6, 129.00 (d)×2, 129.49 (d)×6, 132.38 (s), 140.78 (d), 144.27 (s)×3, 151.77 (s), 165.07 (s), 169.25 (s), 170.93 (s)

MS (FAB) m/z 566 (M+H$^+$, 1), 243 (100)

Optical rotation: L: [α]$^{19}$ −4.3639° (c=13.946, CHCl$_3$), D: [α]$^{19}$+ 2.1802° (c=5.3462, CHCl$_3$).

Example 5-4

Synthesis of Thiazoline Form 18

To the solution of the amide form 17 (44.5 mg, 0.0787 mmol) in dichloromethane (15 ml), Triphenyl phosphine oxide (45.6 mg, 0.164 mmol) and trifluoromethane sulfone acid anhydride (50 µl, 0.297 mmol) ware added under argon atmosphere and stirred at room temperature for 45 minutes. Water (40 ml) was added to the reaction mixture and extracted in chloroform (1×60 ml) and ethyl acetate (2×60 ml). The organic layer was dried over sodium sulfate anhydrite, thereafter concentrated in vacuum. The residue was purified by silica gel column chromatography {20 cm×20 cm×0.5 mm, hexane-ethyl acetate (1:1)} to give the thiazoline form 18 (19.6 mg, 82%) as colorless solid.

Thiazoline Form 18 mp 118-121° C.

IR (film) 1757, 1724 cm$^{-1}$

$^1$H NMR (270 MHz, CDCl$_3$): δ 2.31 (3H, 8), 3.58 (1H, dd, J=9.3, 11.2 Hz), 3.65 (1H, dd, J=9.1, 11.2 Hz), 3.85 (3H, s), 5.22 (1H, dd, J=9.1, 9.3 Hz), 7.04 (1H, d, J=16.1 Hz), 7.12 (2H, d, J=8.6 Hz), 7.13 (1H, d, J=16.1 Hz), 7.51 (2H, d, J=8.6 Hz), $^{13}$C NMR (67.8 MHz, CDCl$_3$): δ 21.15 (q), 34.64 (t), 52.89 (q), 77.96 (d), 122.15 (d)×2, 122.42 (d), 128.69 (d)×2, 132.75 (s), 141.094 (d), 151.66 (s), 169.20 (s), 170.01 (s), 171.17 (s),

MS (EI) m/z 305 (M$^+$., 44), 263 (88), 205 (100), 177 (69), 163 (15), 146 (87), Optical rotation: L: [α]$^{22}$ +9.0924° (c=2.9308, CHCl$_3$), D: [α]$^{22}$ −10.9198° (c=0.4077, CHCl$_3$).

Example 5-5

Synthesis of Analogs 8

The thiazoline form 18 (19.6 mg, 0.0642 mmol) was dissolved in the mixed solution of the ethanol (7 ml) and 10 mM ammoniumbicarbonate in water (28 ml) and a small amount of an esterase of a pig liver was added under argon atmosphere. After stirred at 35 degrees Celsius for 14 hours, the reaction mixture was filtered. And the solution was concentrated in vacuum to give the analog 8 (18.0 mg, quant.) as yellow crystal.

Analogs 8
mp 138-140° C. decomp.
IR (film) 3151, 1626, 1568 cm$^{-1}$
$^1$H NMR (270 MHz, CD$_3$OD): δ 3.52 (1H, dd, J=8.9, 10.9 Hz), 3.61 (1H, dd, J=8.9, 10.9 Hz), 5.01 (1H, t, J=8.9 Hz), 6.80 (2H, d, J=8.9 Hz), 6.91 (1H, d, J=16.0 Hz), 7.10 (1H, d, J=16.0 Hz), 7.42 (2H, d, J=8.9 Hz)
$^{13}$C NMR (67.8 MHz, CD$_3$OD): δ 36.54 (t), 81.19 (d), 116.86 (d)×2, 119.72 (d), 128.00 (s), 130.52 (d)×2, 143.65 (d), 160.70 (s), 171.97 (a), 177.53 (s)
MS (EI) m/z 248 (M$^+$-H, 100), 204 (57), 177 (59), 163 (4), 145 (1)
Optical rotation: L: [α]$^{23}$ +2.2244° (c=1.2462, CH$_3$OH), D: [α]$^{23}$ –2.3653° (c=0.4769, CH$_3$OH).

Example 6-1

Synthesis of Acetyl Form 19

To the solution of the m-hydroxy cinnamic acid (1.80 g, 11.0 mmol) in dichloromethane (200 ml), acetic anhydride (4.0 ml, 42 mmol) and 4-dimethyl aminopyridine (6.70 g, 54.8 mmol) were added. After stirred at room temperature for four hours, water (150 ml) was added to the reaction mixture and extracted in dichloromethane (1×100 ml) and ethyl acetate (2×80 ml). The organic layer was dried over sodium sulfate anhydrite, thereafter concentrated in vacuum. The obtained residue was purified by silica gel column chromatography {Silicagel 200 g, hexane-ethyl acetate (2:1)} to give the acetyl form 19 (1.28 mg, 71%) as a colorless crystal.

Acetyl Form 19
mp 140-142° C., IR (film) 3037, 1761, 1687, 1631 cm$^{-1}$
$^1$H NMR (270 MHz, CDCl$_3$): δ 2.30 (3H, s), 6.44 (1H, br.d, J=15.6 Hz), 7.10-7.35 (3H, complex), 7.71 (1H, br.d, J=15.6 Hz)
$^1$H NMR (270 MHz, CD$_3$OD): δ 2.28 (3H, s), 6.49 (1H, d, J=16.0 Hz), 7.12 (1H, d, J=7.4 Hz), 7.34-7.46 (3H, complex), 7.63 (1H, d, J=16.0 Hz)
$^{13}$C NMR (67.8 MHz, CD$_3$OD): δ 20.91 (q), 121.03 (d), 122.06 (d), 124.55 (d), 12126.64 (d), 130.91 (d), 137.45 (s), 144.75 (s), 152.66 (s), 170.47 (br.s), 170.99 (s)
MS (EI) m/z 206 (M$^+$., 26), 164 (100), 147 (23), 119 (6), 91 (10).

Example 6-2

Synthesis of Amide Form 20

To the solution of the ester form 15 (119.0 mg, 0.315 mmol) in N,N-dimethylformamide (60 ml), acetyl form 19 (133.0 mg, 0.645 mmol), 1-ethyl-3-(3-dimethylamino propyl) carbodiimide hydrochloride (181.2 mg, 0.945 mmol) and 4-dimethyl aminopyridine (197.2 mg, 1.61 mmol) were added under argon atmosphere and stirred at room temperature for two hours. Water (250 ml) was added to the reaction mixture and extracted in a diethyl ether (4×200 ml). The organic layer was dried over sodium sulfate anhydrite, thereafter concentrated in vacuum. The obtained residue was purified by silica gel column chromatography {Silicagel 200 g, hexane-ethyl acetate (3:2)} and further preparative thin layer chromatography {20 cm×20 cm×0.5 mm, 4×; chloroform-ethyl acetate (5:1)} to give the amide form 20 (159.3 mg, 89%) as pale yellow oil.

Amide Form 20
IR (neat) 3283, 1764, 1739, 1663, 1624 cm$^{-1}$
$^1$H NMR (270 MHz, CDCl$_3$): δ 2.31 (3H, s), 2.70 (1H, dd, J=4.8, 12.5 Hz), 2.78 (1H, dd, J=5.4, 12.5 Hz), 3.72 (3H, s), 4.75 (1H, ddd, J=4.8, 5.4, 7.9 Hz), 6.18 (1H, br.d, J=7.9 Hz), 6.33 (1H, d, J=15.6 Hz), 7.09 (1H, dt, J=2.1, 7.1 Hz), 7.17-7.41 (18H, complex), 7.55 (1H, d, J=15.6 Hz)
$^{13}$C NMR (67.8 MHz, CDCl$_3$): δ 21.15 (q), 33.88 (t), 51.22 (d), 52.72 (q), 66.97 (s), 120.61 (d), 121.03 (d), 122.94 (d), 125.45 (d), 126.92 (d)×3, 128.02 (d)×6, 129.47 (d)×6, 129.82 (d), 136.26 (s), 140.70 (d), 144.25 (s)×3, 151.01 (s), 164.88 (s), 169.31 (s), 170.88 (s)
MS (FAB) m/z 566 (M+H$^+$, 1), 243 (100)

Optical rotation: L: $[\alpha]^{23}$ −3.3299° (c=12.254, $CHCl_3$), D: $[\alpha]^{23}$ +4.1534° (c=7.9231, $CHCl_3$).

Example 6-3

Synthesis of the Thiazoline Form 21

To the solution of the amide form 20 (508.1 mg, 0.898 mmol) in dichloromethane (10 ml), triphenyl phosphine oxide (758.0 mg, 2.72 mmol) and trifluoromethane sulfone acid anhydride (0.70 ml, 4.16 mmol) were added under argon atmosphere and stirred at room temperature for five minutes. Water (50) was added to the reaction mixture and extracted with chloroform (3×50 ml). The organic layer was dried over sodium sulfate anhydrite, thereafter concentrated in vacuum. The obtained residue was purified by silica gel column chromatography {20 cm×20 cm×1.75 mm, 2×; hexane-ethyl acetate (1:2)} to give the thiazoline form 21 (93.6 mg, 36%) as a colorless oil.

Thiazoline Form 21

IR (neat) 1768, 1743, 1633 $cm^{-1}$ $^1$H NMR (270 MHz, $CDCl_3$): δ 2.32 (3H, s), 3.58 (1H, dd, J=9.2, 11.2 Hz), 3.65 (1H, dd, J=9.2, 11.2 Hz), 3.82 (3H, s), 5.22 (1H, t, J=9.2 Hz), 7.06-7.10 (3H, complex), 7.21 (1H, m), 7.34-7.42 (2H, complex)

$^{13}$C NMR (67.8 MHz, $CDCl_3$): δ 21.13 (q), 34.65 (t), 52.89 (q), 77.99 (d), 120.62 (d), 122.85 (d), 123.23 (d), 124.91 (d), 129.89 (d), 136.60 (s), 141.07 (d), 151.06 (s), 169.27 (s), 169.84 (s), 171.13 (s)

MS (EI) m/z 305 ($M^+$., 31), 246 (100), 204 (86)

Optical rotation: L: $[\alpha]^{26}$ +6.2401° (c=0.6923, $CHCl_3$), D: $[\alpha]^{18}$ −5.5608° (c=1.1538, $CHCl_3$).

Example 6-4

Synthesis of the Analogs 9

Thiazoline form 21 (38.8 mg, 0.127 mmol) was dissolved in the mixed solution of the ethanol (4 ml) and 10 mM ammoniumbicarbonate in water (16 ml) and a small amount of an esterase of a pig liver was added under argon atmosphere. After stirred at 35 degrees Celsius for 20 hours, the reaction mixture was filtered. And the filtrate was concentrated in vacuum to give the analogs 9 (34.6 mg, quant.) as yellow crystal.

Analogs 9 mp 163-165° C. decomp.

IR 3180, 1583, 1628 $cm^{-1}$ $^1$H NMR (270 MHz, $CD_3OD$): δ 3.54 (1H, dd, J=8.9, 10.9 Hz), 3.63 (1H, dd, J=9.2, 10.9 Hz), 5.05 (1H, dd, J=8.9, 9.2 Hz), 6.79 (1H, ddd, J=1.0, 2.3, 7.9 Hz), 6.99-7.23 (5H, complex)

$^{13}$C NMR (67.8 MHz, $CD_3OD$): δ 36.53 (t), 81.23 (d), 114.66 (d), 118.12 (d), 120.44 (d), 122.89 (d), 131.02 (d), 137.82 (s), 143.45 (d), 159.13 (s), 171.45 (s), 177.05 (s)

MS (EI) m/z 249 ($M^+$., 15), 204 (98), 145 (100).

Example 7

Measurement of the Bioluminescence Spectra

1) Device for Measurement

High Performance Liquid Chromatography (HPLC)

Agilent 1100 series HPLC made by Agilent Technologies Co. Ltd was used. The specification of the device is a degasser, a quarternary pump, a manual injector, a column compartment, a diode array detector, a fluorescence detector and a Chemistation (software for PCs). The used column is CHIRALCEL OD-RH manufactured by Daicel Chemical Industries, Ltd. (0.46 cm inside diameter, 15 cm in length).

pH Measurement

F-23 type glass electrodehydrogen ion concentration manufactured by Horiba, Ltd.-style hydrogen-ion concentration instructions meter was used.

Quantity of Luminescent Photon Measurement

They were measured using Luminescencer-PSN AB-2200 manufactured by ATTO Co., Ltd.

Measurement of Luminescent Spectrum

They were measured using feeble luminescence fluorescent spectra device AB-1850 manufactured by ATTO Co., Ltd. All the measured spectra were the spectra which calibrated with the characteristic of the detector.

2) Reagents

The ultra pure water was collected from Milli-RX12α manufactured by MILLIPORE and used it. For methanol and t-butanol, the special grade solvent manufactured by Kanto Chemical Co., Ltd. was used.

For the luciferase (derived from *Photinus pyralis* of North America product firefly), was used the recombination type manufactured by Sigma-Aldrich Corporation or Promega KK.

For ATP-Mg the product manufactured by Sigma-Aldrich Corporation was used.

For the phosphate-buffered saline, a hydrogenphosphate dipotassium 12 hydrate (special grade) and a dihydrogenphosphate potassium 0.2 hydrate (special grade) manufactured by Wako Pure Chemical Industries, Ltd. were dissolves in the ultra pure water and adjust the pH and used it.

A potassium t-butoxide manufactured by Tokyo Kasei Kogyo Co., Ltd was used.

For a distilled water and an acetonitrile, a solvent for high performance liquid chromatography manufactured by Kanto Chemical Co., Ltd. was used.

A trifluoroacetic acid (special grade) manufactured by Wako Pure Chemical Industries, Ltd. were used.

3) Preparation of Samples

Substrate Solution

The Substrate was weighted with an electronic balance, and it was diluted. The phosphate-buffered saline (50 mM, pH 6.0) was used in the case of the chemiluminescence measurement, and t-butanol was used in the case of the bioluminescence as a solvent.

Enzyme Solution

The luciferase was diluted with Tris-HCl buffer solution (50 mM, pH 8.0 s) to become 1 μg/μl and divided. This was used as stocked solution, so that was diluted to be used each time. Note that, the stock solutions were stored in a freezer of −80 degrees Celsius.

ATP-Mg Solution

ATP-Mg was diluted in the ultra pure water.

Bioluminescence Spectrum

The solution of a potassium phosphate buffer (0.5 M, pH 8.0, 20 μl), the solution of substrate (2.5 mM, 20 μl) and enzyme solution (20 μl), then ATP-Mg solution (ten mM, 40 μl) were mixed in a 200 μL of a polystyrene tube, and measured the luminescent spectrum. The enzyme solution was used at the concentration of 17 μM, provided that enzymes at 1.7 μM and at 170 μM were used in the firefly luciferin (1) and the phenol type luciferin respectively. The exposure time for the measurement of the luminescent spectrum was 60 seconds, provided that the firefly luciferin was five seconds.

Result of the Experiment

Figure 1:
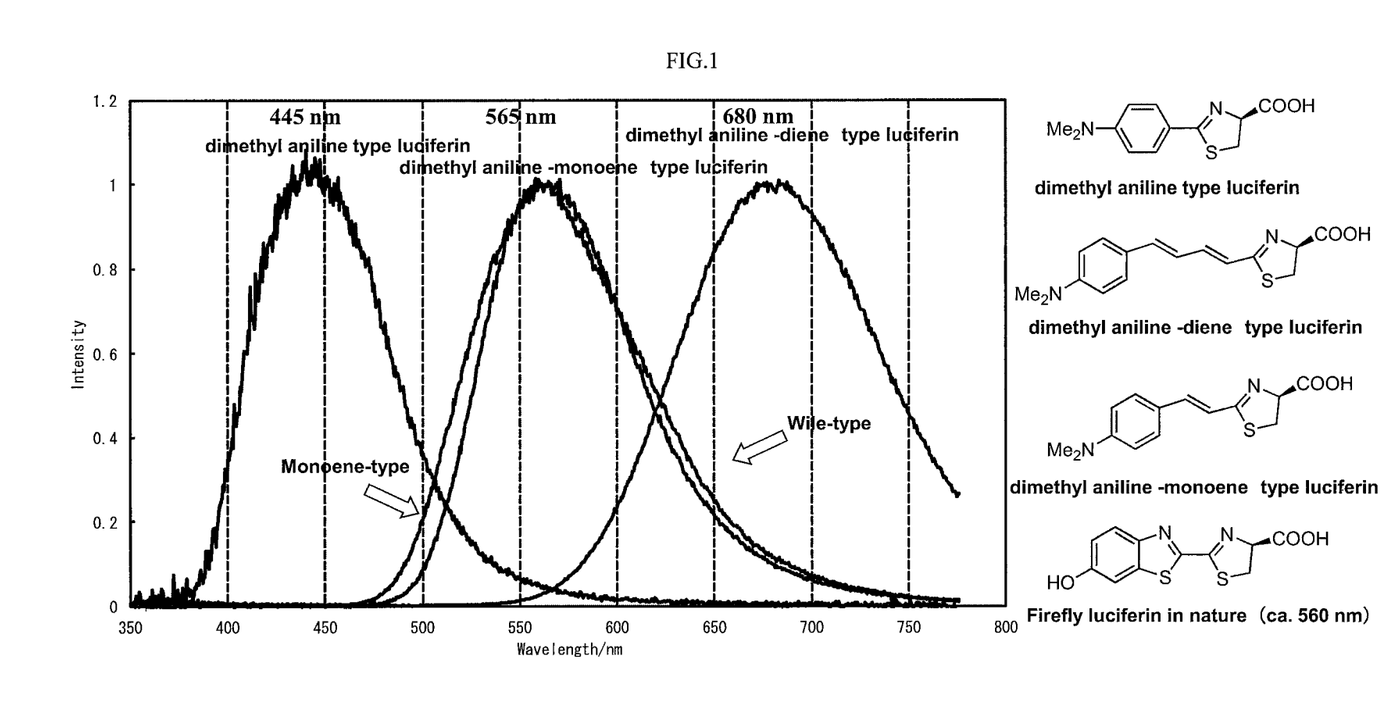
FIG. 1 shows bioluminescent spectra by the compound of the present invention.
Figure 2:
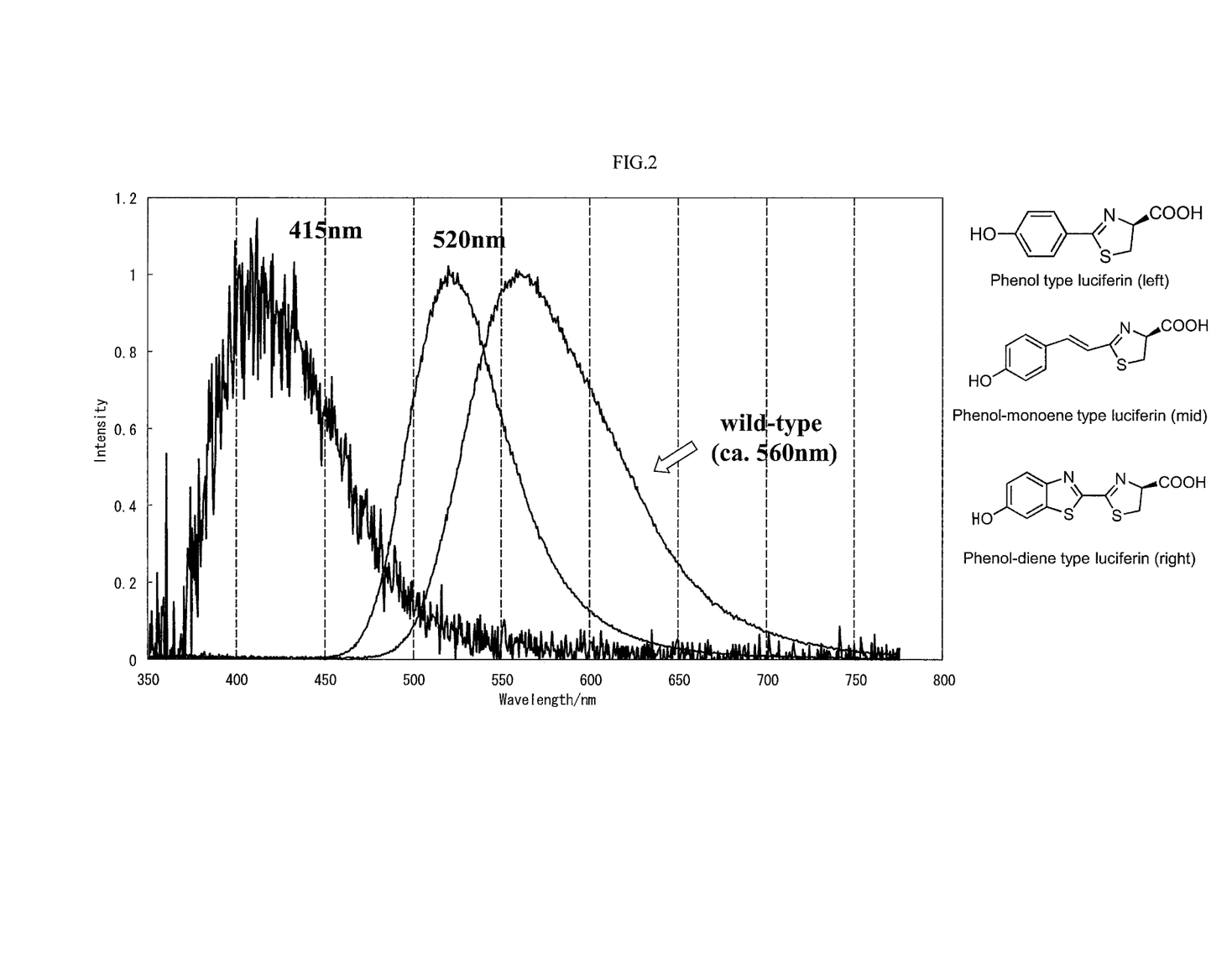
FIG. 2 shows bioluminescent spectra by the luciferin analogs.

It was revealed that the firefly luciferin analogs II, III and IV of the present invention were the substrate which produce the luminescence of 445 nm, 565 nm and 680 nm according to the above experiment (see FIG. 1). On the other hand, for the phenol type firefly luciferin analogs rather than the aniline type, the analogs 9 did not luminescent. The analogs 7 and analogs 8 had luminescent activity for luminescent wavelength of 415 nm and 520 nm respectively (see FIG. 2).

On the other hand, the analogs Dimethyl aniline part was Me- and an acetyl did not have the activity. Therefore, the change of the bioluminescence was not able to be detected.

Discussion

The compound of above formulas II, III and IV are corresponding to the colors of blue, yellow green and red as indicated in FIG. 1 respectively. Therefore, the luminescence corresponding to RGB which is three primary colors of the light can be achieved by using the firefly luciferin analogs of the present invention. The blue which is a short wavelength than 450 nm and the red which is a longer wavelength than 650 nm are the luminescent wavelength region which were not able to be achieved in the existing firefly bioluminescent system.

The compound of above formulas II, III and IV also are very easy to synthesize them compared to a luciferin in natural.

It is also considered that the chain length of the olefin moiety contributes to the change of the wavelength from the result of experiments. About wavelength of 120 nm is changed by adding one double bond in the luminescent substrate of the dimethyl aniline type of the present invention. Therefore, it is considered that the compound which has the luminescent peak at the side of the longer wavelength can be made by regulating the number of double bond. Furthermore, it seems that the luminescence peak of the substrate which has similar structure by regulating the distance between the a moiety which have a benzene ring (left of the formula I) and the heterocycle moiety (right of the formula) according to this knowledge. Therefore, the luminescence peak may be controlled by regulating the number of double bond for the luminescent substrate wherein-$NR_1R_2$ part is substituted for other substituent, even if they are other than dimethyl aniline type.

The invention claimed is:

1. A heterocycle compound of the formula:

or a salt thereof.

2. A kit for detecting an luminescence comprising a compound according to claim 1 with ATP and $Mg^{2+}$.

3. A method for detecting an luminescence comprising:
reacting a compound according to claim 1 with luminescent beetle luciferase, and detecting an luminescence from the compound.

* * * * *